United States Patent

Ebeling et al.

[11] Patent Number: 5,466,910
[45] Date of Patent: Nov. 14, 1995

[54] METHOD OF TESTING WELD SEAMS USING AN EDDY-CURRENT TECHNIQUE

[75] Inventors: Wilhelm Ebeling, Rohr; Guy Faber, Oberrohrdorf; Gottfried Kuhnen, Oberrohrdrof; Arthur Scholz, Wettingen, all of Switzerland

[73] Assignee: ABB Management AG, Baden, Switzerland

[21] Appl. No.: 338,763

[22] Filed: Nov. 10, 1994

[30] Foreign Application Priority Data

Nov. 22, 1993 [DE] Germany .......................... 43 39 720.4

[51] Int. Cl.⁶ ............................................... B23K 9/095
[52] U.S. Cl. ....................................... 219/130.01; 228/104
[58] Field of Search ........................ 219/130.01, 124.34; 228/104; 324/209

[56] References Cited

U.S. PATENT DOCUMENTS 4,588,873  5/1986  Fenn et al. .
4,665,734  5/1987  Joet .
4,712,722  12/1987  Hood et al. ................. 228/104

FOREIGN PATENT DOCUMENTS 2909649  9/1979  Germany .
2905034  8/1980  Germany .

OTHER PUBLICATIONS

"Method for Inspecting Welded Part by Eddy Current Flaw Detection", Patents Abstracts of Japan, P–683, Apr. 2, 1988, vol. 12/No. 100, Patent No. 62–232558 of Oct. 13, 1987.

*Primary Examiner*—Clifford C. Shaw
*Attorney, Agent, or Firm*—Burns, Doane, Swecker & Mathis

[57] ABSTRACT

In a method of testing weld seams using an eddy-current technique, large-volume and coarse-grained weld seams are subjected to the testing, said weld seams being tested for the presence of faults in layers on-line during their buildup. The method is particularly suitable for testing components with austenitic weld metal. It is notable for a high fault location probability.

3 Claims, 1 Drawing Sheet

METHOD OF TESTING WELD SEAMS USING AN EDDY-CURRENT TECHNIQUE

BACKGROUND OF THE INVENTION

1. Field of the Invention

The invention relates to a method of testing weld seams using an eddy-current technique, which method can be used, in particular, for fault location in components whose weld metal has a coarse-grained microstructure which cannot be made finer by a heat treatment.

2. Discussion of Background

Very high requirements are imposed on weld seams in relation to freedom from faults. Possible faults are fusion defects (side-wall defects, root defects or interrun fusion defects), pores, cracks (in the weld or alongside it), slag enclosures and undercuts.

The welding is therefore usually followed by a preliminary test before the workpieces are given a stress-relief anneal and the weld seam is subjected to a final test.

Various methods are known for assessing welded joints, for example magnetic stray-flux testing, radiographic irradiation testing and the pulse-echo technique using ultrasound.

The location of internal faults, for example cracks, with the aid of X-ray or gamma radiation presents difficulties in weld seams if the thickness of the weld seam is very great, since only those faults can be detected whose size is at least 2 to 3% of the workpiece thickness. The radiographic method is also ruled out if the weld seam is difficult to reach. In these cases, ultrasonic testing and magnetic stray-flux testing are left as test methods, magnetic stray-flux testing being restricted, however, to magnetizable materials and to the surface region of the test pieces. Consequently, often only ultrasonic testing is open to discussion.

One problem in the ultrasonic testing of workpieces and, consequently, also of weld seams may lie in the grain size. If the wavelength of the ultrasound is very much greater than the grain size, the microstructure grain is, to a certain extent, missed by the sound. If, however, the grain size is approximately ⅒ of the wavelength of the ultrasound or even greater, the scattering of the sound which occurs may render testing of the weld seam impossible. That is the case, for example, for austenitic weld seams.

Specifically, the scattering phenomena not only reduce the level of the echoes, but also generate many smaller echoes which result in an irregular interfering background against which the echoes of the defective points stand out only indistinctly or not at all.

An increase in the ultrasonic power (higher transmission voltage) or a signal amplification provide no improvement in this connection since the interfering background increases to the same extent as the echoes which are of interest. If the test frequency is reduced as an alternative, that is to say the wavelength is increased, then, although microstructural conditions having a somewhat greater grain size can be tested using ultrasound, the detection sensitivity for small defect points decreases.

From practical experience it is known that thick-walled TIG-welded pipes are examined for the occurrence of hot cracks in the weld seam and in the heat-affected zone using optical methods by magnifying and imaging the weld seam on a monitor. The disadvantages of this method are that only those cracks can be detected which extend to the surface and that the inspection is very time-consuming and is very fatiguing for the test operator.

A further known method for determining microstructure inhomogeneities is magnetic induction testing. If a metallic workpiece is introduced into an alternating magnetic field generated by a coil, eddy currents are induced in the workpiece and the said eddy currents generate, in turn, a magnetic field which is opposed to the field of the coil. If there are cracks, pores or other inhomogeneities in the workpiece, the eddy currents have to flow round these obstructions, with the result that the secondary magnetic field and, consequently, the secondary voltage are affected. In the case of long workpieces, for example pipes, the self-comparison method is used, but in this method neither the crack length nor the crack depth can be determined in the case of continuous longitudinal cracks. If exploration coils are used for crack testing, then, although the crack depth can be determined if certain conditions are observed, the method is suitable only for the subsurface region of workpieces and, consequently, not for thick workpieces and thick weld seams.

The abovementioned methods also have the disadvantage that the weld seams can be tested only after their complete fabrication and, consequently, substantial throughput times occur. On-line testing of large-volume weld seams having close correlation with the fault size is unknown.

SUMMARY OF THE INVENTION

Accordingly, one object of the invention is to avoid all these disadvantages and to develop a novel method of testing weld seams using an eddy-current technique which is suitable for locating faults in large multi-layer weld seams whose weld metal has a coarse-grained microstructure which cannot be made finer by a heat treatment, which test method does not require much time.

According to the invention this is achieved in that, in the testing of large-volume and coarse-grained weld seams, the latter are tested in layers on-line during their buildup.

The advantages of the invention are to be seen, inter alia, in the fact that, because of the low material volume to be tested, a high resolving power is achieved and, consequently, relatively small faults, for example short cracks, can be detected and in the fact that even coarse-grained materials can be tested satisfactorily. Both these aspects substantially increase the fault-location probability in comparison with the ultrasonic testing normally used.

It is particularly expedient if the testing is performed already at elevated workpiece temperatures above room temperature, preferably at workpiece temperatures of up to 350° C., because the weld seam does not then have to be cooled to room temperature. This shortens the throughput time.

The method is advantageously applied in the welding of austenitic parent materials using austenitic welding wire or only in the case of welding using austenitic welding wire, in which cases a coarse-grained austenitic weld metal is produced by the welding.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein there is shown an exemplary embodiment of the invention based on the welding of a rotor for a turbine.

The figures diagrammatically shows the method sequence according to the invention.

Figure 3:
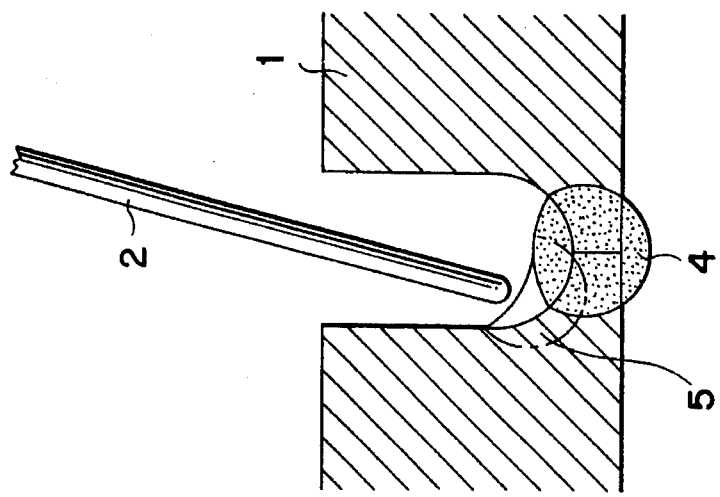
FIG. 3 shows an additional welding step following the test step of FIG. 2.
Figure 2:
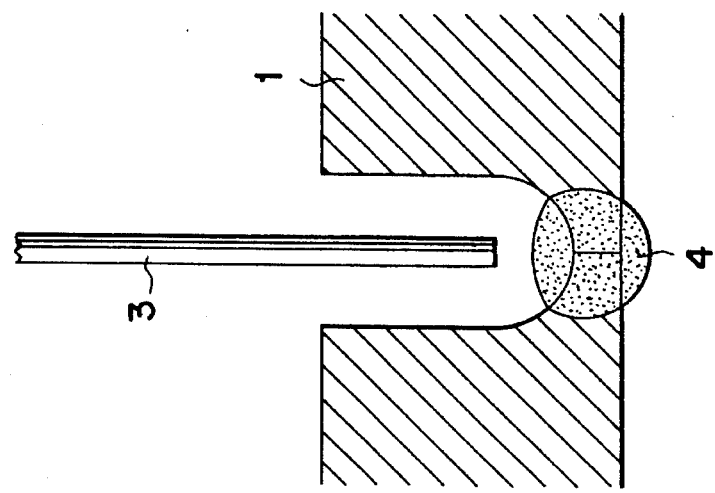
FIG. 2 shows a test step following the welding step of FIG. 1.

Only those elements are shown which are essential to an understanding of the invention.

DETAILED DESCRIPTION

Refering now to the drawings, wherein like reference numerals designate identical or corresponding parts throughout the several views, the invention is explained in greater detail with reference to an exemplary embodiment.

Figure 1:
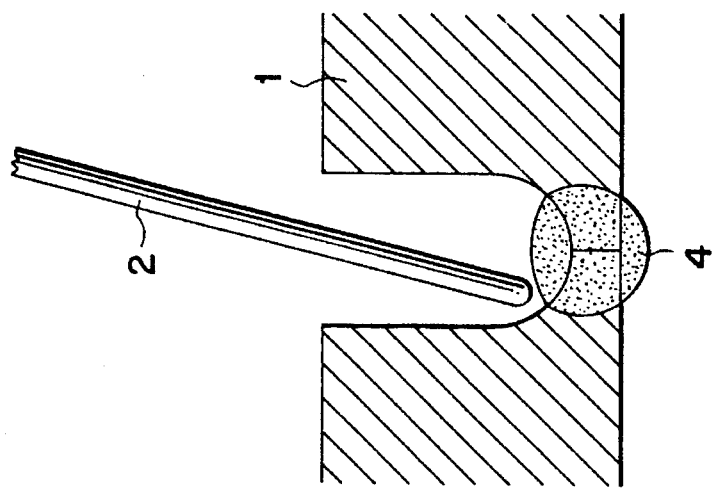
FIG. 1 shows a welding step in accordance with the method of the invention.

In this exemplary embodiment, the rotor 1 is composed of an austenitic material, for example 17 Cr 14 Ni 3 W, the remainder being Fe. As shown in FIG. 1, welding carried out with the aid of an austenitic welding wire 2, for example 16 Cr 12 Ni 1 Mo, the remainder being Fe. Because of the workpiece thickness, a multilayer and large-volume weld seam has to be fabricated and the weld seam has a very coarse-grained and anisotropic microstructure because of the material used. The surface geometry of the weld seam is very uneven because of its multilayer nature.

Heat treatment of the rotor 1 after the welding operation in order to remove the coarse grain and the anisotropy is impossible.

After the first layer 4 has been welded, it is immediately subjected, according to the invention, to an on-line test using an eddy-current method illustrated by FIG. 3. For this purpose, the probe 3 of the test instrument is presented to the surface of the first weld layer 4, the weld layer 4 is scanned with the probe 3 and, during this process, it is subjected to a magnetic induction test known per se.

Since the depth of penetration into the austenitic materials is several millimeters and noise effects due to the coarse grain as in the case of ultrasonic testing do not occur here, a fault location probability is achieved which is markedly higher than in the case of ultrasonic testing after the complete filling of the welding grooves. The location probability for crack-type defective points is particularly high if such defective points extend to the surface.

If no faults are indicated, the probe 3 is removed and the second layer 5 is welded, as indicated by FIG. 5, and the entire operation repeated.

In this way, the preliminary testing of the entire weld seam can be eliminated and the throughput time for fabricating the workpiece, in this case the welded rotor 1, is reduced.

It is furthermore possible to apply the test method described above even if the temperature of the workpiece bulk to be tested is increased. The weld pass does not therefore have to be cooled to room temperature before testing, with the result that the throughput time is also additionally shortened in this way.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of testing large volume, coarse-grain size weld seams during a welding operation, comprising the steps of:

(a) applying a layer on a weld seam in a workpiece;

(b) scanning a surface of the layer as it is formed with an eddy-current probe coil, wherein the workpiece is at a temperature of up to 350° C.;

(c) determining a location of defects in the first layer from an output signal of the probe;

(d) applying an additional layer to the weld seam; and (e) repeating steps (b), (c) and (d) until the weld is completed.

2. The method as claimed in claim 1, wherein the workpiece is formed of austenitic materials.

3. The method as claimed in claim 1, wherein the weld is formed using an austenitic weld material.

\* \* \* \* \*